United States Patent [19]
Stern et al.

[11] Patent Number: 5,223,256
[45] Date of Patent: Jun. 29, 1993

[54] THROMBOLYTICALLY ACTIVE NON-GLYCOSYLATED PROTEIN

[75] Inventors: Anne Stern, Penzberg; Ulrich Kohnert, Habach; Rainer Rudolph, Weilheim; Stephan Fischer, Polling; Ulrich Martin, Mannheim, all of Fed. Rep. of Germany

[73] Assignee: Boehringer Mannheim GmbH, Mannheim-Waldhof, Fed. Rep. of Germany

[21] Appl. No.: 585,129

[22] PCT Filed: Feb. 6, 1990

[86] PCT No.: PCT/EP90/00194
 § 371 Date: Sep. 28, 1990
 § 102(e) Date: Sep. 28, 1990

[87] PCT Pub. No.: WO90/09437
 PCT Pub. Date: Aug. 23, 1990

[30] Foreign Application Priority Data
 Feb. 7, 1989 [DE] Fed. Rep. of Germany ....... 3903581

[51] Int. Cl.$^5$ .............. C12N 15/58; C12N 9/64; A61K 37/547; A61K 37/54
[52] U.S. Cl. .............. 424/94.63; 435/252.33; 435/320.1; 435/226; 435/69.6; 536/23.2; 424/94.64; 935/14
[58] Field of Search ........... 435/212, 219, 226, 252.33, 435/240.2, 252.3, 320.1, 172.3; 530/412, 414, 417, 418, 404, 402; 536/27; 424/94.63, 94.64

[56] References Cited

U.S. PATENT DOCUMENTS

| | | | |
|---|---|---|---|
| 4,511,502 | 4/1985 | Builder et al. | 260/112 R |
| 4,620,948 | 11/1986 | Builder et al. | 530/419 |
| 4,753,879 | 6/1988 | Rosa et al. | 435/172.3 |
| 4,766,075 | 8/1988 | Goeddel et al. | 435/240.2 |
| 4,777,043 | 10/1988 | Bennett et al. | 424/94.64 |
| 4,898,825 | 2/1990 | Morii et al. | 435/212 |
| 4,908,205 | 3/1990 | Bennett et al. | 424/94.64 |
| 4,933,434 | 6/1990 | Rudolph et al. | 530/405 |
| 4,935,237 | 6/1990 | Higgins et al. | 424/94.64 |
| 4,963,357 | 10/1990 | Bell et al. | 424/94.64 |
| 4,978,620 | 12/1990 | Morii et al. | 435/226 |
| 5,034,225 | 7/1991 | Bennett et al. | 424/94.64 |
| 5,037,752 | 8/1991 | Bell et al. | 435/226 |
| 5,073,494 | 12/1991 | Heyneker et al. | 435/226 |

FOREIGN PATENT DOCUMENTS

| | | |
|---|---|---|
| 8804319 | 2/1989 | Denmark . |
| 112122 | 6/1984 | European Pat. Off. . |
| 219874 | 4/1987 | European Pat. Off. . |
| 302456 | 2/1989 | European Pat. Off. . |

OTHER PUBLICATIONS

Saito, Y. et al., *Annals New York Academy of Sciences*, vol. 613:452–454, 1990.
World Patent Index Abstract, Accession No. C89-017728 for Niwa et al. patent family including EPO 302456 and DK 8804319.
Heussen, C. et al., *J. Biol. Chem.*, 259 (19):11635–11638, 1984.
Scopes, R. K. *Protein Purification*, Springer-Verlag, New York, 1987, pp. 15–20 and 133–144.
Cleary, S. et al., *Biochemistry*, 25:1884–91, 1989.

*Primary Examiner*—Garnette D. Draper
*Assistant Examiner*—Marianne Porta Allen
*Attorney, Agent, or Firm*—Felfe & Lynch

[57] ABSTRACT

A new thrombolytically active protein is not glycosylated and consists of the following amino acid sequence:

```
  1 SYQGNSDCYF  GNGSAYRGTH  SLTESGASCL
                PWNSMILIGK  VYTAQNPSAQ
 51 ALGLGKHNYC  RNPDGDAKPW  CHVLKNRRLT
                WEYCDVPSCS  TCGLRQYSQP
101 QFRIKGGLFA  DIASHPWQAA  IFAKHRRSPG
                ERFLCGGILI  SSCWILSAAH
151 CFQERFPPHH  LTVILGRTYR  VVPGEEEQKF
                EVEKYIVHKE  FDDDTYDNDI
201 ALLQLKSDSS  RCAQESSVVR  TVCLPPADLQ
                LPDWTECELS  GYGKHEALSP
251 FYSERLKEAH  VRLYPSSRCT  SQHLLNRTVT
                DNMLCAGDTR  SGGPQANLHD
301 ACQGDSGGPL  VCLNDGRMTL  VGIISWGLGC
                GQKDVPGVYT  KVTNYLDWIR
351 DNMRP
``` or said amino acid sequence with an additional N-terminal methionine. DNA sequences encoding the thrombolytically active, non-glycosylated protein and pharmaceutical compositions containing said protein are also disclosed. The protein possesses particularly favorable properties when used to dissolve blood clots.

6 Claims, 7 Drawing Sheets

THROMBOLYTICALLY ACTIVE NON-GLYCOSYLATED PROTEIN

The present invention concerns a new thrombolytically active protein, a DNA sequence which codes for the new thrombolytically active protein, expression plasmids which contain a DNA sequence which codes for the thrombolytically active protein as well as a process for the preparation of such plasmids, a process for the production of the thrombolytically active protein and an agent for dissolving blood clots which contains the thrombolytically active protein.

Coagulated blood contains polymeric fibrin which is the main component of the protein matrix. Fibrin is dissolved under physiological conditions by a fibrinolytic system in a reaction cascade which is similar to that of blood coagulation. The central reaction in this is the activation of plasminogen to plasmin which is for example mediated by the tissue-type plasminogen activator t-PA. Plasmin, in turn, dissolves fibrin which is the main component of the protein matrix of coagulated blood. The enzymatic activity of natural t-PA or t-PA obtained from eukaryotes by genetic engineering, i.e. the catalytic activation of plasminogen to plasmin, is very low in the absence of fibrin or fibrinogen cleavage products, but it can be substantially increased in the presence of these proteins, namely by more than ten-fold.

T-PA is cleaved by proteases present in the blood into an A-chain and a B-chain. Both parts of the chain remain bound via a cysteine-bridge. The ability to stimulate the activity of t-PA is a significant advantage in comparison with other known plasminogen activators such as, for example urokinase or streptokinase (cf. for example M. Hoylaerts et al., J. Biol. Chem. 257 (1982), 2912-2919; W. Nieuwenhuizen et al., Biochem. Biophys. Acta, 755 (1983), 531-533).

The mechanism of action of t-PA in vivo is described for example in Korniger and Collen, Thromb. Hämostasis 46 (1981), 561-565. The focus of enzymatic activity on the fibrin surface would seem to make it a suitable agent for the treatment of pathological vascular occlusions (for example myocardial infarction) which has been confirmed to a large extent by clinical trials (Collen et al., Circulation 70 (1984), 1012; Circulation 73 (1986), 511).

A disadvantage of t-PA is however the rapid decrease in its plasma concentration (clearance). As a result, a relatively large amount of t-PA is necessary to achieve an effective lysis of thrombi. On the other hand, high therapeutic doses result in side effects such as for example bleeding.

A natural degradation product of t-PA is described in EP 0 196 920 which only contains the kringle II and protease domains, and whose N-terminus begins with alanine 160 (enumeration system according to the amino acid sequence cited by Pennica et al. in Nature 301 (1983), 214–221).

The clearance rate of this product of t-PA degradation does not, however, differ significantly from that of the natural t-PA. Only a chemical modification of the catalytic domain via attachment of a blocking group can result in an improvement.

It is therefore the object of the present invention to modify t-PA such that the resultant derivative has a much reduced clearance rate and thus a longer half-life in blood plasma. In this process the ability to lyse thrombi as well as the ability to be stimulated by fibrin should be preserved.

The embodiment of the present invention is therefore a tissue-type plasminogen activator (t-PA derivative) which is characterized in that it is not glycosylated and consists of the following amino acid sequence:

(M)

| | | | | | |
|---|---|---|---|---|---|
| 1 | SYQGNSDCYF | GNGSAYRGTH | SLTESGASCL | PWNSMILIGK | VYTAQNPSAQ |
| 51 | ALGLGKHNYC | RNPDGDAKPW | CHVLKNRRLT | WEYCDVPSCS | TCGLRQYSQP |
| 101 | QFRIKGGLFA | DIASHPWQAA | IFAKHRRSPG | ERFLCGGILI | SSCWILSAAH |
| 151 | CFQERFPPHH | LTVILGRTYR | VVPGEEEQKF | EVEKYIVHKE | FDDDTYDNDI |
| 201 | ALLQLKSDSS | RCAQESSVVR | TVCLPPADLQ | LPDWTECELS | GYGKHEALSP |
| 251 | FYSERLKEAH | VRLYPSSRCT | SQHLLNRTVT | DNMLCAGDTR | SGGPQANLHD |
| 301 | ACQGDSGGPL | VCLNDGRMTL | VGIISWGLGC | GQKDVPGVYT | KVTNYLDWIR |
| 351 | DNMRP | | | | | which can be extended by M at the amino end i.e. at the amino acid No. 1=S.

It was established that, surprisingly, deletion of the other domains which are present in native t-PA had no effect on the thrombolytic efficacy of the protein and that the fibrin-dependent stimulatability of the mutein was comparable to that of native t-PA. Although it was determined that the thrombolytically active protein according to the present invention lacked the property to bind to fibrin it however, surprisingly, exhibited a thrombolytic efficacy in vivo which was even much improved compared to that of native t-PA Equally surprising is the fact that when a dose is administered which is sufficient for an effective thrombolysis the systemic fibrinolysis remains almost unaffected. It has therefore been demonstrated that under physiological conditions the thrombolytically active protein according to the present invention shows the typical t-PA property of fibrin specificity. These results were obtained from pharmacological investigations of the thrombolytically active protein according to the present invention (see Examples 6 and 7). In addition, the protein according to the present invention has a very high specific activity. By using the described renaturation procedure activities of 500 to 800 kU/mg have already been measured.

A further embodiment of the present invention is a DNA sequence which codes for the thrombolytically active protein according to the present invention and contains the following sequence:

```
   1 ATGTCTTACCAAGGAAACAGTGACTCCTACTTTGGGAATGGGTCAGCCTACCGTGGCACG      60
  61 CACAGCCTCACCGAGTCGGGTGCCTCCTGCCTCCCGTGGAATTCCATGATCCTGATAGGC     120
 121 AAGGTTTACACAGCACAGAACCCCAGTGCCCAGGCACTGGGCCTGGGCAAACATAATAC     180
 181 TGCCGGAATCCTGATGGGGATGCCAAGCCCTGGTGCCACGTGCTGAAGAACCGCAGGCTG     240
 241 ACGTGGGAGTACTGTGATGTGCCCTCCTGGTCCACCTGCGGCCTGAGACAGTACAGCCAG     300
 301 CCTCAGTTTCGCATCAAAGGAGGGCTCTTCGCCGACATCGCCTCCCACCCCTGGCAGGCT     360
 361 GCCATCTTTGCCAAGCACAGGAGGTCGCCCGGAGAGCGGTTCCTGTGCGGGGGCATACTC     420
 421 ATCAGCTCCTGCTGGATTCTCTCTGCCGCCCACTGCTTCCAGGAGAGGTTTCCGCCCCAC     480
 481 CACCTGACGGTGATCTTGGGCAGAACATACCGGGTGGTCCCTGGCGAGGAGGAGCAGAAA     540
 541 TTTGAAGTCGAAAAATACATTGTCCATAAGGAATTCGATGATGACACTTACGACAATGAC     600
 601 ATTGCGCTGCTGCAGCTGAAATCGGATTCGTCCCGCTGTGCCCAGGAGAGCAGCGTGGTC     660
 661 CGCACTGTGTGCCTTCCCCCGGCGGACCTGCAGCTGCCGGACTGGACGGAGTGTGAGCTC     720
 721 TCCGGCTACGGCAAGCATGAGGCCTTGTCTCCTTTCTATTCGGAGCGGCTGAAGGAGGCT     780
 781 CATGTCAGACTGTACCCATCCAGCCGCTGCACATCACAACATTTACTTAACAGAACAGTC     840
 841 ACCGACAACATGCTGTGTGCTGGAGACACTCGGAGCGGCGGGCCCCAGGCAAACTTGCAC     900
 901 GACGCCTGCCAGGGCCATTCGGGAGGCCCCCTGGTGTGTCTGAACGATGGCCGCATGACT     960
 961 TTGGTGGGCATCATCAGCTGGGGCCTGGGCTGTGGACAGAAGGATGTCCCGGGTGTGTAC    1020
1021 ACAAAGGTTACCAACTACCTAGACTGGATTCGTGACAACATGCGACCG                 1068
```

The DNA sequence according to the present invention serves to express the thrombolytically active protein according to the present invention when it is present on an expression plasmid. An expression plasmid of this kind is a further embodiment of the invention as well as an expression plasmid with a different DNA sequence which, however, also codes for the thrombolytically active protein according to the present invention. Due to the degeneracy of the genetic code sequences which differ from the DNA sequence shown are suitable for this purpose.

Besides the sequence coding for the thrombolytically active protein the expression plasmid preferably also contains a promotor structure which can be regulated (e.g tac), an efficient terminator (e.g. fd), a selection marker (e.g. β-lactamase-gene) and an origin of replication.

A further embodiment of the present invention is the plasmid pA27.3. The preparation of this plasmid is described in Example 1; it contains a DNA sequence which codes for the thrombolytically active protein according to the present invention.

Yet a further embodiment of the invention is a process for the construction of one of the expression plasmids according to the present invention, wherein a DNA sequence which codes for the thrombolytically active protein according to the present invention or a derivative thereof which contains further regions of the t-PA protein in addition to the kringle II and the protease domains is incorporated into a plasmid and those domains which code for amino acids which are not present in the thrombolytically active protein according to the present invention are deleted by site-directed mutagenesis.

The choice of plasmids into which the DNA sequence coding for the thrombolytically active protein according to the present invention is to be incorporated, is dependent on the host cells which are later to be used to express the derivative. Suitable plasmids, as well as the minimum requirements for such a plasmid (e.g. origin of replication, restriction site) are known to the expert. Within the scope of the invention a cosmid, the replicative double-stranded form of phages (λ, M13), and other vectors known to the expert can be used instead of a plasmid. The method of site-directed mutagenesis is described by Morinaga et al., Biotechnolgy 21, (1984), 634, and is carried out essentially as described.

Yet a further embodiment of the invention is a process for the production of a thrombolytically active protein according to the present invention, which is characterized in that one of the plasmids according to the present invention is expressed in suitable host cells and the product is isolated from the culture medium, if necessary after lysis of the host cells. Prokaryotic cells are preferably used as the host cells to produce the thrombolytically active protein according to the present invention. In this connection, it is particularly preferable to first separate the so-called "inclusion bodies" (insoluble protein aggregates) which form during this process from the soluble cell particles, to solubilize the inclusion bodies containing t-PA by treatment with guanidine hydrochloride under reducing conditions, and then to derivatise with GSSG and finally to renature the t-PA derivative by addition of L-arginine and GSH. Exact instructions for the activation of t-PA from "inclusion bodies" are for example described in EP-A 0 219 874 and EP-A 0 241 022. According to the present invention any other method for the isolation of the active protein from inclusion bodies can, however, be employed as well.

In the process according to the present invention one works preferably in the presence of L-arginine, in particular in a concentration of 10 to 1,000 mmol/l for the purification of K2P.

The removal of foreign proteins according to the present invention by affinity chromatography is carried out in a preferred embodiment of the invention over an ETI (Eritrina Trypsin Inhibitor) adsorber column. In this connection, ETI is fixed on a carrier material (adsorber) such as e.g. Sepharose. The purification over an ETI adsorber column has the advantage that the ETI adsorber column material can be loaded directly with the concentrated renaturation preparation even in the presence of such high concentrations of arginine as 0.8 mol/l arginine. In this way, an aggregation of K2P, which can occur at low arginine concentrations under 10 mmol/l, is avoided. Thus, it is especially preferred to carry out the purification of K2P over an ETI adsorber column in the presence of 0.6 to 0.8 mol/l arginine. In this process the solution containing the K2P has preferably a pH of over 7, particularly preferably of 7.5 to 8.6.

The elution from the ETI column is effected by lowering the pH in the presence as well as absence of arginine under conditions which allow a good solubility of K2P. Preferably the pH value is in the acid range during the elution, particularly preferably in the range of 3 to 5.5.

A K2P produced according to the present invention has a specific t-PA activity of 550,000±200,000 IU/mg with a purity of more than 95%, preferably of more than 99%.

Thus, according to the present invention a thrombolytically active protein is provided which has a significantly longer plasma half-life due to the reduced clearance rate. The derivative according to the present invention does not, however, lose any of its properties which appear to make it suitable as a therapeutic agent for thrombolysis of arterial and venous thrombi. On the contrary, the dose necessary for a thrombolytic therapy with K2P can be reduced to at least a quarter of the usual dose for native t-PA. With equipotent doses of K2P and native t-PA, the coagulation system is affected less by K2P than by native t-PA and the bleeding time is significantly extended in contrast to native t-PA so that complications of bleeding which occur in the therapy with K2P can possibly be reduced.

The thrombolytically active protein according to the present invention is therefore particularly suitable for use in a pharmaceutical agent which again is a further embodiment of the present invention. When the t-PA according to the present invention is used as a pharmaceutical agent it is only necessary to administer a significantly smaller dose than is the case for native t-PA produced in CHO.

The invention is elucidated by the following examples in conjunction with the FIGURES.

EXAMPLE 1

Construction of the Plasmid pA27.3

The starting plasmid pREM7685, described in EP-A 0 242 836 contains the following components: tac-promotor, lac-operator region with an ATG-start codon, the region coding for the t-PA derivative FK2P, the transcription terminator from pKK223-3, a β-lactamase gene, a kanamycin-resistance gene and the origin of the plasmid pACYC177, a plasmid which is present in the cell in a small copy number. The sequence of the t-PA derivative FK2P is composed of the nucleotides 190–336 (F-domain), 715–1809 (K2-domain, protease, small portion of 3'UT) and an ATG-start codon. The nucleotide positions are quoted according to the sequence described by Pennica et al., Nature 301 (1983) 214–221.

For the deletion of the F-domain from the FK2P-construction in plasmid pREM7685 the method of Morinaga et al., Biotechnology 21 (1984), 634 was essentially used. Two fragments were isolated from pREM7685 for heteroduplex formation. Fragment A: pREM7685 was cleaved with the restriction enzyme EcoRI. The cleavage products were separated by gel electrophoresis and the largest EcoRI fragment was eluted from the gel. Fragment B: plasmid pREM7685 was linearized with the restriction enzyme XhoI. The linearized plasmid was also obtained preparatively by gel electrophoresis. The following oligonucleotide was prepared synthetically for the mutagenesis:

5' TG TCT TAC CAA GGA AAC AGT GA 3'

In order to form the heteroduplex, fragment A, fragment B (450 fmol of each) and the oligonucleotide (75 pmol) were mixed and incubated initially for 3 minutes at 100° C. in the presence of 50 mmol/l NaCl, 10 mmol/l Tris-HCl, pH 7.5 and 10 mmol/l MgSO4 and then transferred immediately onto ice. The renaturation of the DNA was carried out for 30 minutes at 60° C. The following were added to the heteroduplex for repair synthesis:

Deoxynucleotide triphosphate (0.25 mmol/l), ATP (1 mmol/l), NaCl (100 mmol/l), Tris-HCl, pH 7.5 (6.5 mmol/l), MgCl2 (8 mmol/l), β-mercaptoethanol (1 mmol/l), Klenow-fragment of the DNA-polymerase from E. coli (0.125 U/μl reaction mixture) and T4-ligase (0.1 U/μl reaction mixture). The repair synthesis was carried out for 4 hours at 16° C. Subsequently, this preparation was transformed into *E. coli* cells (RM82, DSM 3689) with a lac I⁹-plasmid and the transformed cells were selected by the addition of 25 μg/ml kanamycin to the culture medium.

Figure 1:
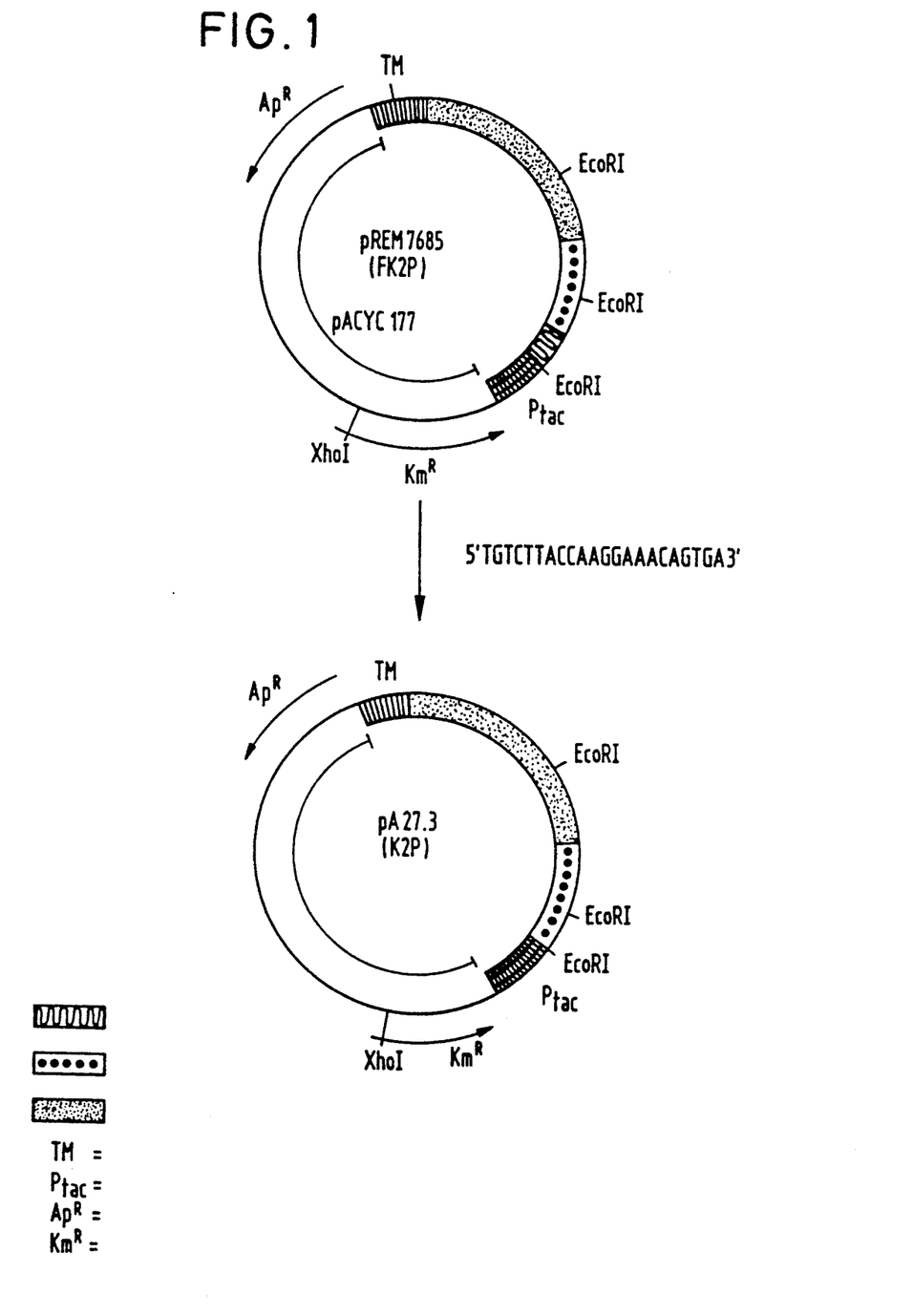
FIG. 1 shows schematically the construction of plasmid pA27.3.

Those clones which contain the plasmid pA27.3 which encode the thrombolytically active protein K2P according to the present invention were selected by the colony hybridisation technique using the mutagenesis oligonucleotide described above as a probe. This plasmid differs from the starting plasmid pREM7685 inter alia by the absence of a PstI or a SspI cleavage site. Both these cleavage sites are contained in the region of the starting plasmid which codes for the F-domain. The construction of the plasmid pA27.3 is shown schematically in FIG. 1.

EXAMPLE 2

Preparation of Active Thrombolytically Active Protein K2P from *E. coli*

Cell Lysis and Preparation of the Inclusion Bodies (IB's)

1.6 kg cell wet-weight (*E. coli*, DSM 3689, transformed with plasmid pA27.3) was suspended in 10 l 0.1 mol/l Tris-HCl, 20 mmol/l EDTA, pH 6.5, 4° C. 2.5 g lysozyme was added to this and incubated for 30 minutes at 4° C.; afterwards complete cell lysis was carried out by high pressure dispersion. 5 l 0.1 mol/l Tris-HCl, 20 mmol/l EDTA, 6% Triton X100 and 1.5 mol/l NaCl, pH 6.5 was mixed with the lysate solution and incubated for a further 30 minutes at 4° C. Following this the inclusion bodies (IB's) were separated by centrifugation in a Padberg centrifuge.

The pellet was suspended in 10 l 0.1 mol/l Tris-HCl, 20 mmol/l EDTA, pH 6.5, incubated for 30 minutes at 4° C. and the IB-preparation was isolated by subsequent centrifugation.

Solubilization of the IB's 100 g IB's (wet-weight) were suspended in 450 ml 0.1 mol/l Tris-HCl, 6 mol/l guanidine·HCl, 0.2 mol/l DTE (1,4 dithioerythritol), 1 mmol/l EDTA, pH 8.6 and stirred for 2.5 hours at 25° C.

After adjustment of the pH to pH 3 with HCl (25%), the solution was dialyzed against 10 mmol/1 HCl (3×50 l, 24 hours, 4° C.).

Derivatization

Guanidine·HCl (solid) was added in such a quantity that after final dilution of the above dialysate with 10 mmol/1 HCl the guanidine-HCl concentration was 6 mol/1.

The preparation was preincubated for 1.5 hours at 25° C., afterwards the oxidized glutathione (GSSG) concentration was adjusted to 0.1 mol/1 and the Tris-HCl concentration to 0.05 mol/1 and the pH was titrated with 5 mol/1 NaOH to pH 9.3. The preparation was stirred for 3.5 hours at 25° C.

After adjustment of the pH to pH 3 with HCl (25%) the solution was dialyzed against 10 mmol/1 HCl (3×100 l, 48 hours, 4° C.). After the dialysis the preparation was centrifuged and the clear supernatant was processed further.

Renaturation

A 10 l reaction vessel was filled with 0.1 mol/1 Tris-HCl, 0.8 mol/1 L-arginine, 2 mmol/1 GSH (glutathione, reduced form), 1 mmol/1 EDTA, pH 8.5. The renaturation was carried out at 20 C by a three-fold addition of 100 ml derivative (mixed disulphide, see above) at 24 hour intervals.

After the renaturation a preparation was obtained with a specific activity of 1500 to 10000 IU/mg (determination cf Example 4b). The unit IU is a unit of the activity according to the definition of the WHO, National Institute for Biological Standards and Control.

Concentration of the Renaturation Preparation

The renatured preparation can, if required, be concentrated on a haemodialyzer.

EXAMPLE 3

Purification of K2P from *E. coli*

1. Purification of K2P from *E. coli* by Affinity Chromatography on ETI-Sepharose After Previous Concentration a) Elution with citric acid The renaturation preparation was concentrated 1:23 on a haemodialyzer (Asahi AM 300) and supplemented with 0.5 mol/l NaCl. 550 ml concentrate of the reoxidation preparation was applied (10 column volumes per hour, 10 CV/h) to an ETI (Erythrina-Trypsin-Inhibitor)-Sepharose column (V=50 ml) which was equilibrated with 0.1 mol/l Tris-HCl, pH 7.5, 0.8 mol/l arginine, 0.5 mol/l NaCl and washed with the equilibration buffer until the absorbance of the eluate at 280 nm reached the blank value for the buffer. The bound material was eluted with 20 mmol/l citric acid, pH 3.2.

|  | Volume (ml) | Activity (IU/ml) | $C_{Prot.}$ (mg/ml) | SA[1] (IU/mg) |
|---|---|---|---|---|
| concentrate | 550 | 57162 | 14 | 4083 |
| ETI-eluate | 90 | 330000 | 0.71 | 465000 |

[1]specific activity: activity in chromogen test (cf Example 4b) divided by protein content of the sample b) Elution with 0.3 mol/l arginine, pH 4.5

The renatured preparation was concentrated as described in Example 3.1.a). 800 ml of the concentrate was applied to an ETI-Sepharose column (25 ml; 12 CV/h) which was equilibrated with 0.1 mol/l Tris-HCl, pH 7.5, 0.8 mol/l arginine, 0.5 mol/l NaCl and washed with the equilibration buffer until the absorbance of the eluate at 280 nm reached the blank value for the buffer. The bound material was eluted with 0.3 mol/l arginine, pH 4.5.

|  | Volume (ml) | Activity (IU/ml) | $C_{Prot.}$ (mg/ml) | SA (IU/mg) |
|---|---|---|---|---|
| concentrate | 800 | 20000 | 11.3 | 1770 |
| ETI-eluate | 55 | 280000 | 0.6 | 550000 |

2. Purification of K2P from *E. coli* by Affinity Chromatography on ETI-Sepharose Without Previous Concentration 12 l of the reoxidation preparation was applied to an ETI-Sepharose column (V=10 ml) which was equilibrated with 0.1 mol/l Tris-HCl, pH 7.5, 0.8 mol/l arginine, 0.5 mol/l NaCl and washed with the equilibration buffer until the absorbance of the eluate reached the absorbance of the buffer. The bound material was eluted with 0.8 mol/l arginine, pH 5.

|  | Volume (ml) | Activity (IU/ml) | $C_{Prot.}$ (mg/ml) | SA (IU/mg) | F[1] |
| --- | --- | --- | --- | --- | --- |
| reoxidation-preparation | 12000 | 615 | 0.135 | 4556 | 25 |
| ETI-eluate | 42 | 105000 | 0.185 | 568000 | 35 |

[1]F: stimulation by fibrin = activity in the presence of fibrin divided by activity without fibrin

EXAMPLE 4

Characterization of Purified K2P from E. coli

SDS-PAGE and Reversed-Phase HPLC

The homogeneity of the preparation purified by affinity chromatography on ETI-Sepharose was demonstrated by SDS-PAGE and reversed-phase HPLC (RP-HPLC). From the relative mobilities the molecular weight of K2P from prokaryotes was calculated at 38,500+2,000 Da. The densitometric analysis showed a purity of the preparation of >95%.

RP-HPLC is based on the different interactions of proteins with hydrophobic matrices. This property was used as an analytical method to quantify the degree of purity.

The analysis of the purified K2P from E. coli was carried out on a Nucleosil 300 separation column (Knauer) using a trifluoroacetic acid/acetonitrile gradient (buffer A: 1.2 ml trifluoroacetic acid in 1,000 ml $H_2O$; buffer B: 300 ml $H_2O$, 700 ml acetonitrile, 1 ml trifluoroacetic acid; 0 to 100%). Integration of the chromatographic analysis yielded a purity of >95%.

N-terminal amino acid sequence

The N-terminal amino acid sequence was determined using an ABI 470 sequencer with a standard programme and on-line PTH detection. The determined sequence S1-Y2-Q3-G4-N5-S6-D7-C8-Y9 agreed with the expected sequence deduced from the DNA-sequence.

b) Activity Determination

The in vitro activity of K2P from E. coli was determined according to the test instructions in the "Zeitschrift für die gesamte innere Medizin" (ZGIMAL) 42 (17) 478–486 (1987). The specific activity was 550,000 IU/mg±200,000 IU/mg. The stimulatability of K2P from E.coli in this test system by BrCN-fibrinogen fragments (activity in the presence of fibrinogen fragments divided by activity in the absence of fibrinogen fragments) was >25.

c) In Vitro Binding to Fibrin

The in vitro binding of K2P from E. coli to fibrin was determined according to the method described by Higgins and Vehar (D. L. Higgins, G. A. Vehar, Biochem. 26, (1987) 7786-7791).

Figure 2:
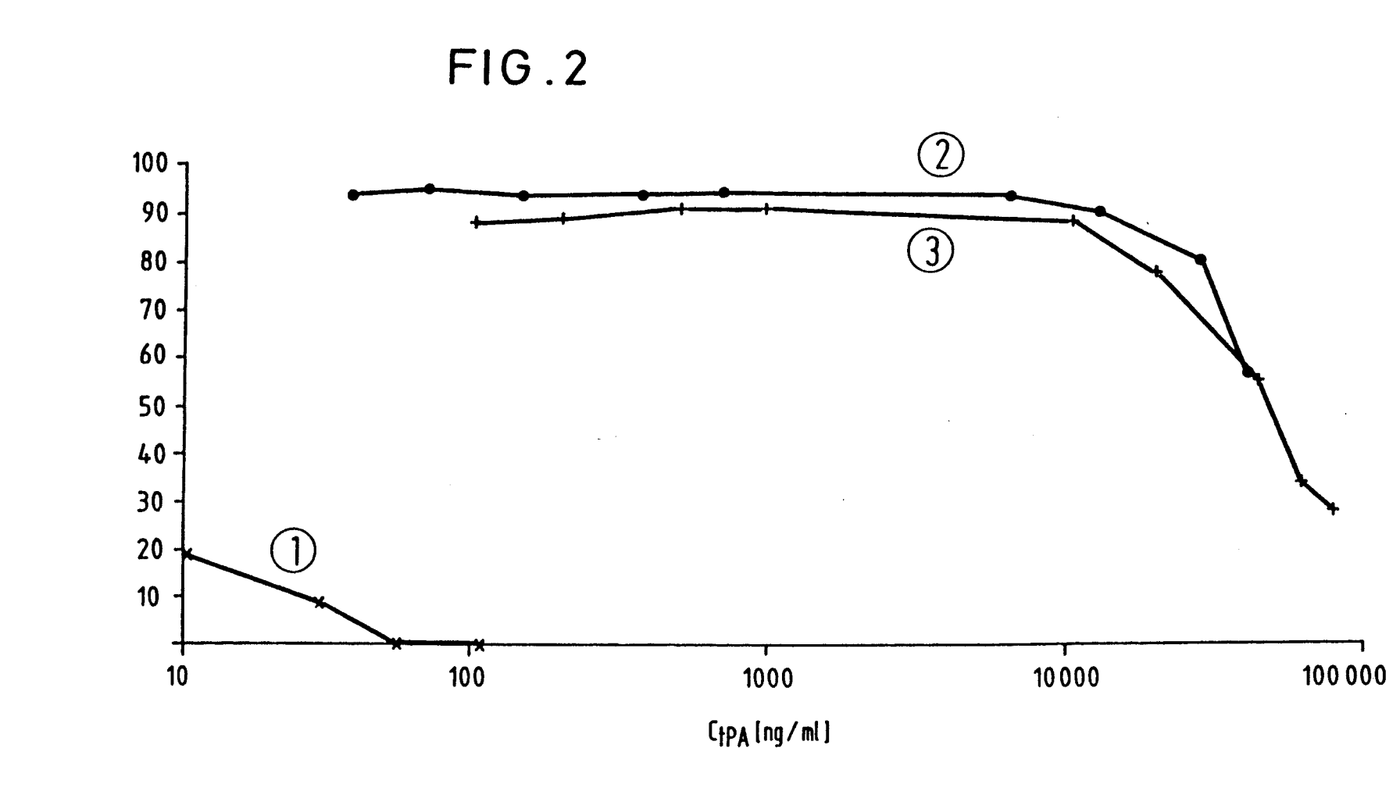
FIG. 2 shows a comparison of fibrin binding of the thrombolytically active protein (curve 1) according to the present invention with that of native t-PA expressed in CHO cells (double-stranded t-PA from CHO cells, cleaved at the physiological cleavage site Arg 275-Ile276, curve 2) and single-stranded t-PA from CHO cells, (curve 3)
Figure 3:
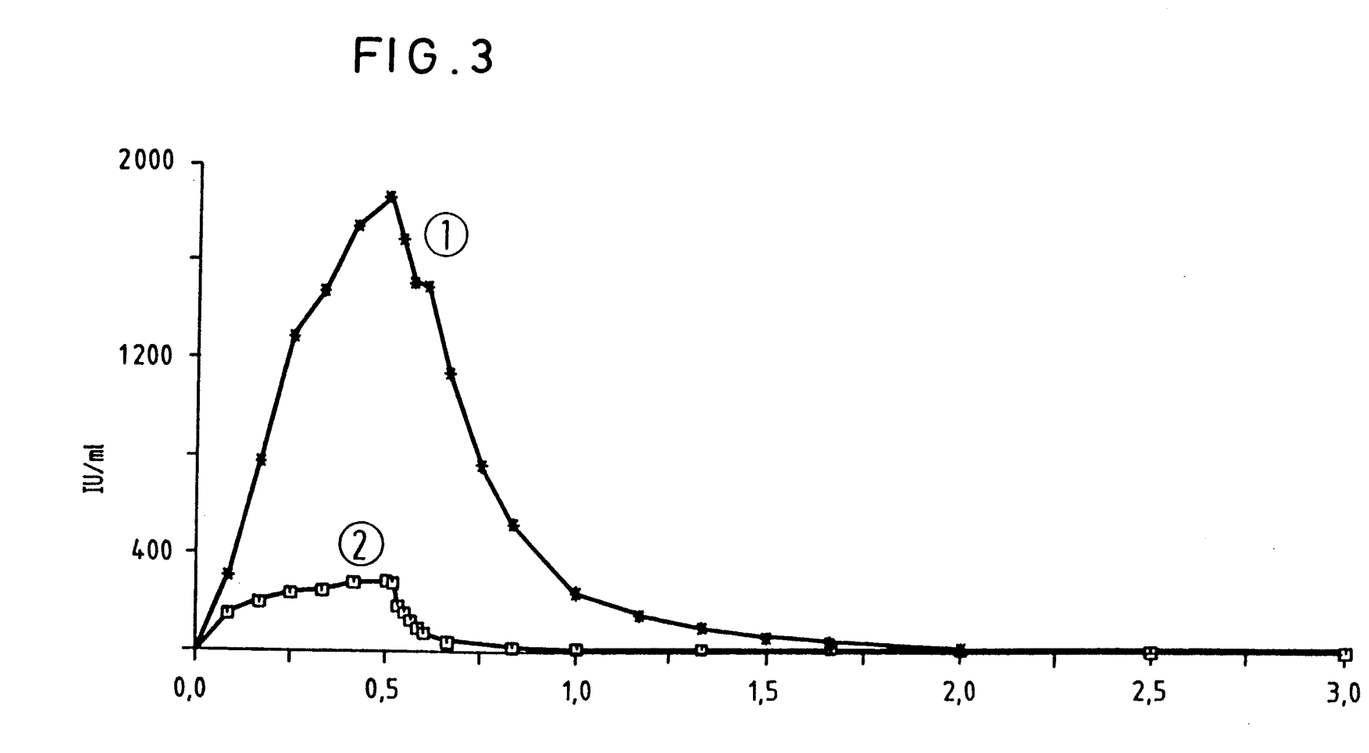
FIG. 3 and FIG. 4 show diagrams of the pharmacokinetics of t-PA activity of the thrombolytically active protein according to the present invention compared to a commercially available t-PA preparation (Actilyse ®); (curve 1: K2P, dose 200,000 U/kg =0.25 mg/kg I.V. inf. for 30 min.; number of animals investigated (rabbits): 4; curve 2: Actilyse ®; dose 200,000 U/kg; I.V. inf. for 30 min., number of animals investigated (rabbits): 6).
Figure 4:
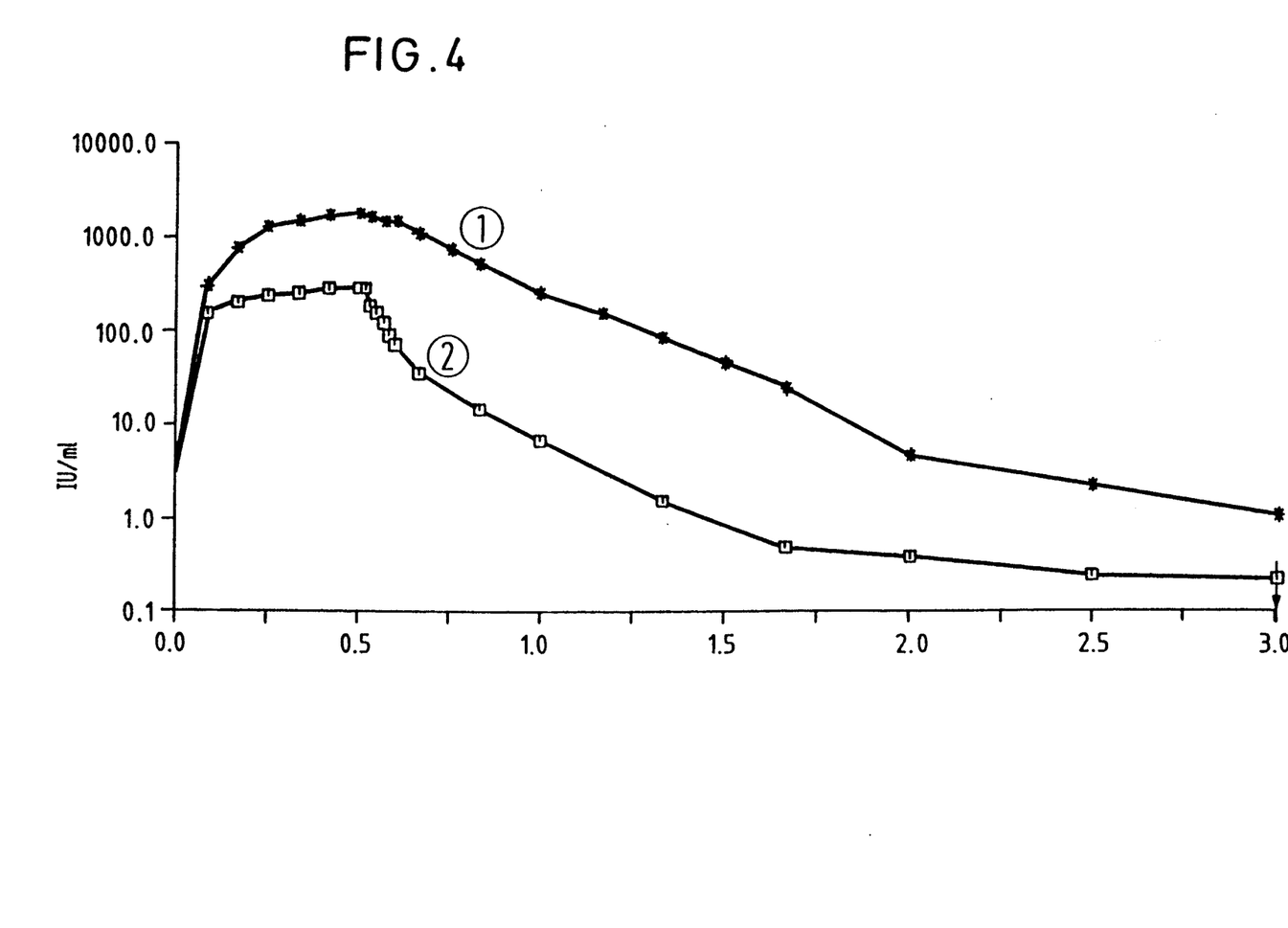

FIG. 2 shows that K2P from E.coli compared to t-PA from CHO or t-PA from E.coli shows no significant binding to fibrin.

EXAMPLE 5

To increase the yield of expression product, the sequence encoding the K2P-gene was subcloned in a plasmid with a high copy number. Plasmid pePA 126.1 described in the patent application DE 38 38 378.0 was used for this. This plasmid is composed mainly of the vector pKK223-3 and the t-PA coding sequence as described in EP-A 0 242 835.

An fd-terminator sequence was first integrated into this plasmid. For this, the plasmid pePa 126.1 was linearized with the restriction enzyme Hind III. The plasmid cleaved in this manner was separated by gel electrophoresis and isolated preparatively. The plasmid pLBUI (Beck et al., (1978), Nucl. Acids. Res., 5, 4495–4503; Gentz et al., (1981) PNAS 78 (8):4963) was cleaved with Hind III and a Hind III fragment of about 360 bp which contained the fd-terminator was isolated preparatively by gel electrophoresis and gel elution. The linearized plasmid pePA 126.1 and the 360 bp Hind III fragment from pLBUI were ligated. The ligation preparation was cotransformed with the plasmid pUBS 500, described in the application DE 38 38 378.0, in E. coli, DSM 2102 . From the clones, those were selected that contained the desired plasmid pePA 126 fd which differs from the starting plasmid pePA 126.1 in that it contains a second Hind III cleavage site.

Two fragments were isolated from the plasmid pePA 126 fd: a BamHI/PvuI-fragment of 3.4 kb size and a PvuI/XmaI fragment of 1.3 kb size. Both these fragments were ligated with a BamHI/XmaI fragment of about 1.3 kb from plasmid pA27.3 and transformed with the plasmid pUBS 500 into E. coli. The resultant plasmid was named pA27 fd and can be distinguished from pePA 126 fd in that in a restriction digest with EcoRI the second smallest EcoRI fragment from pePA 126 fd of about 610 bp length is about 515 bp shorter in pA27 fd.

EXAMPLE 6

Pharmacological Results of the Thrombolytically Active Protein K2P Expressed in Prokaryotes 1. Pharmacokinetics of K2P in Rabbits The pharmacokinetic properties of K2P were compared to those of Actilyse ® in New-Zealand white rabbits. Both fibrinolytic agents were infused for 30 minutes at a dose of 200,000 IU/kg body weight. Plasma samples were taken at defined times before, during and after the infusion. The t-PA activity was measured with a spectrophotometric test according to J. H. Verheijen et al., (Thromb. Haemostas. 48, 266, 1982), modified according to H. Lill (Z. ges. Inn. Med. 42, 478, 1987).

A calculation programme for non-linear regression modified according to H. Y. Huang (Aero-Astronautics-Report 64, Rice University, 1-30, 1969) was used to calculate the pharmacokinetic parameters. The parameters were calculated individually using a bi-exponential pharmacokinetic model.

Figure 5:
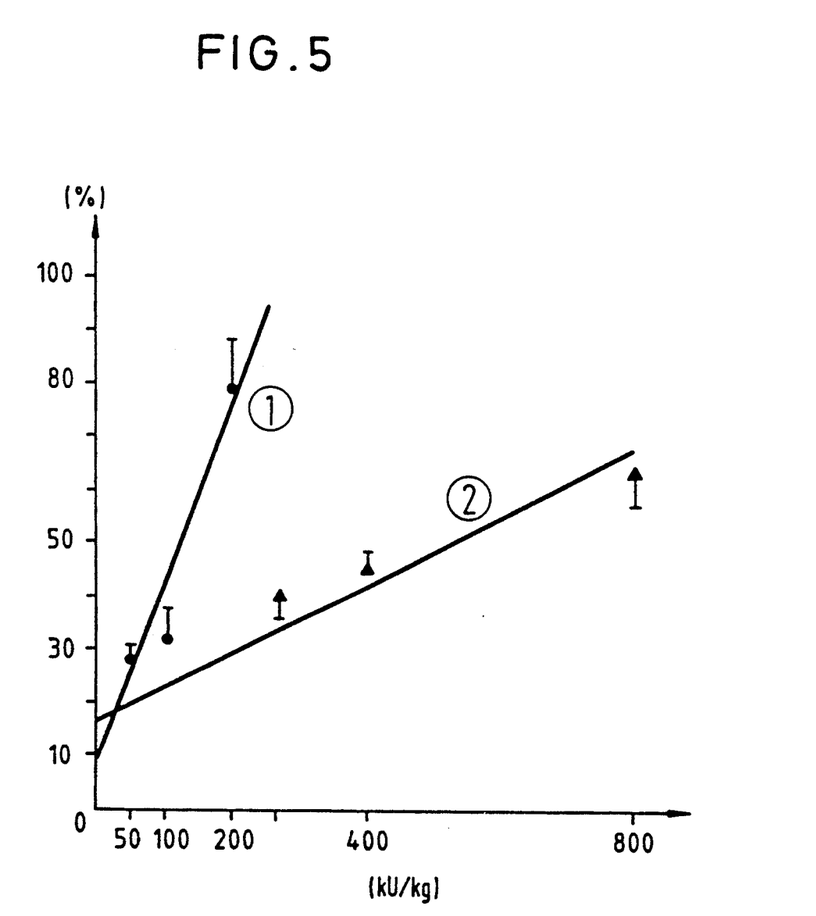
FIG. 5 shows dose-response curves (of rabbits) for thrombolysis for the thrombolytically active protein according to the present invention in comparison with Actilyse ® (shown is the mean value+SEM, 1 kU $\triangleq$ 1,000 IU; curve 1: K2P; curve 2: Actilyse ®).
Figure 6:
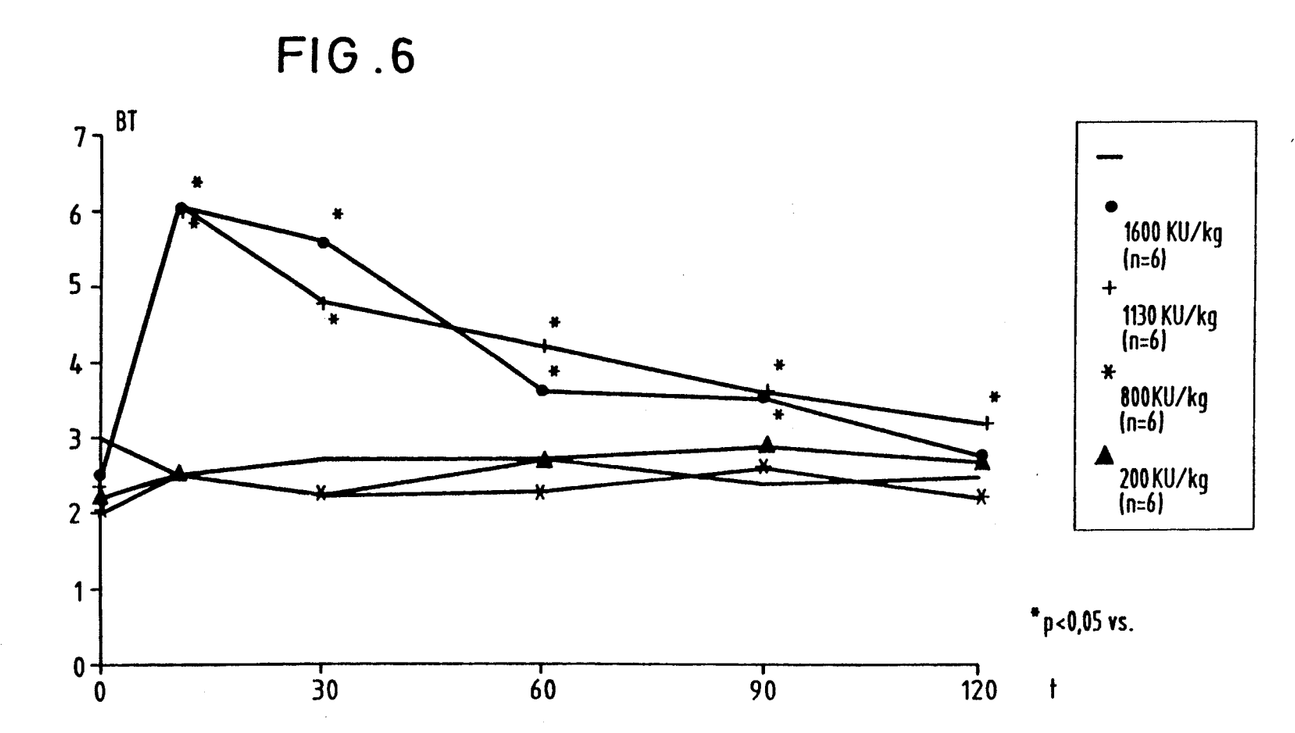
FIG. 6 shows the time course for Simplate bleeding time (BT) before and after an i.v. bolus injection of placebo or increasing doses of Actilyse ® in anaesthetised dogs.

K2P exhibits a five-fold longer half-life ($t1/2\alpha = 10.3$ min, reduction of concentration in plasma) than Actilyse ® (t-PA preparation of the Thomae company) (Table 1, FIGS. 5 and 6). At the end of the infusion (after 30 min) with K2P-Pro a plasma concentration of t-PA activity ($C_{inf}$) of 1986 IU/ml was measured which was thus six-fold higher than that obtained with Actilyse ®. The volume of distribution of the central compartment ($V_c$) was 46.8 ml/kg for K2P compared to 73.7 ml/kg for Actilyse ®. The total plasma clearance ($Cl_{tot}$) of K2P-Pro was reduced to 1/7 ($Cl_{tot}=3.2$ ml/min/kg) compared to Actilyse ® ($Cl_{tot}=22.2$ ml/min/kg). When administering a fibrinolytic agent as a bolus injection "the area under the curve" (AUC) is of particular interest since it allows a comparison of the time-course of the prevailing plasma concentration. K2P has an eight-fold higher AUC (1,064 IU/ml×h) than Actilyse ® (133.3 IU/ml×h).

K2P shows on the whole a five- to eight-fold better pharmacokinetic profile at the same dose in comparison to Actilyse®, the only recombinant t-PA-protein which is commercially available at present.

2. Pharmacodynamics of K2P in Rabbits

The jugular vein model established by D. Collen et al., (J. Clin. Invest. 71, 368, 1983) was used to investigate the thrombolytic efficacy. K2P and Actilyse® were each examined at three dose levels. The fibrinolytic agents were infused for 4 hours and afterwards the rate of thrombolysis was determined (Table 2, FIG. 5).

With the aid of linear regression lines the dose for a 50% rate of thrombolysis (ED50) was calculated to be 124,000 IU/kg body weight for K2P and 520,000 IU/kg body weight for Actilyse. K2P thus shows a four-fold higher thrombolytic activity than Actilyse.

K2P attained a dose-dependent plasma concentration of t-PA activity which, at a four-fold lower dose, was comparable with Actilyse®. A dose of 200 kU K2P/kg body weight which has a comparable thrombolytic activity to 800 KU Actilyse®/kg body weight had slight effects on the coagulation parameters fibrinogen, plasminogen and $\alpha_2$-antiplasmin which do not differ from the effects of a dose of 800 kU Actilyse®/kg body weight.

K2P is a thrombolytically active protein which has the same thrombolytic activity as Actilyse® in the jugular vein thrombosis model of the rabbit in a 4 hour infusion of the thrombolytic agent when the dose is reduced to a quarter of the Actilyse® dose. K2P at this reduced dose does not differ from Actilyse® in its effects on the coagulation system and in the plasma concentration of the t-PA activity.

examine the thrombolytic effect of K2P from *E. coli* on arterial thrombi. The dog was chosen as the animal species. The method for the formation of a coronary artery thrombus was a modification of the technique of Romson et al., (Thromb. Res. 17, 841, 1980). In the open thorax of anaesthetized dogs which were artificially respirated, the intimal surface of the ramus branch of the left circumflex coronary artery (LCX) was electrically stimulated (150 µA) and by this means a thrombus was produced. Previously a screw was applied distal to the thrombosis in order to eliminate a reactive hyperaemia by the experimental stenosis. Proximal to the coronary thrombosis the LCX was equipped with an electromagnetic flow measuring head in order to be able to measure the reperfusion.

In a study to determine the dosage, BM 06.022 with the eukaryotic t-PA (Alteplase, Actilyse®, Dr. Karl Thomae GmbH, Biberach, FRG) in four different doses and with placebo were injected as an initial single intravenous bolus over 1 min into heparinized dogs; 6 animals were injected with each dose. Plasma samples were taken before and at defined times after the injection in order to determine the plasma concentration of the t-PA activity and of fibrinogen, plasminogen and $\alpha_2$-antiplasmin as well as the number of thrombocytes in whole blood. Fibrinogen was measured coagulometrically according to Clauss (Acta haemat. 17, 237, 1957), plasminogen and $\alpha_2$-antiplasmin were measured spectrophotometrically as described by Collen et al., (J. Clin. Invest. 71, 368, 1983). In addition, the "Simplate bleeding time" was measured on the hind leg of the dogs using a lancet (Simplate® I, Organon Teknika, Eppelheim, FRG) during a venostasis of 40 mm Hg (J. Surg. Res. 27, 244, 1979). The statistical comparison of

TABLE 1

Pharmacokinetic parameters derived from computer calculations of the t-PA plasma concentrations - time data based on t-PA-activity

| Agent (Dose: 200000 IU/kg bw) | $t_{½\alpha}$ (min) | $t_{½\beta}$ (min) | $C_{inf}$ (IU/ml) | $V_C$ (ml/kg) | $Cl_{tot}$ (ml/min/kg) | $AUC_{extrapol.}$ $\left(\frac{IU}{ml} \cdot h\right)$ |
|---|---|---|---|---|---|---|
| K2P | 10.3 | 14.9 | 1986.6 | 46.8 | 3.2 | 1064.4 |
| (n = 4) | ±1,7 | ±4,6 | ±762,6 | ±14,7 | ±1,1 | ±443,2 |
| Actilyse® | 2,1 | 10,9 | 326,6 | 73,7 | 22,2 | 133,3 |
| (N = 6) | ±0,6 | ±2,4 | ±118,1 | ±19,7 | ±7,6 | ±44,1 |

TABLE 2

Thrombolysis, level of t-PA plasma activity (at the end of a 4 h infusion) and haemostasis parameters (30 min after the end of the infusion) of K2P, Actilyse® and solvent

| | K2P 200 kU/kg | K2P 100 kU/kg | K2P 50 kU/kg | Solvent NaCl/Tween | Actilyse® 800 kU/kg | Actilyse® 400 kU/kg |
|---|---|---|---|---|---|---|
| Thrombolysis (%) | 79 ± 9 (n = 3) | 32 ± 6 (n = 5) | 29 ± 1 (n = 2) | 11 ± 1 (n = 6) | 64 ± 6 (n = 7) | 46 ± 3 (n = 6) |
| Plasma t-PA activity (IU/ml) | 93,7 ± 18,2 | 44 ± 3 | 7 ± 0 | — | 107 ± 27 | 47 ± 9 |
| Fibrinogen (%) | 74 ± 2 | 90 ± 6 | 86,5 ± 6 | 92 ± 3 | 77 ± 6 | 90 ± 3 |
| Plasminogen (%) | 79 ± 7 | 75 ± 6 | 87 ± 11 | 98 ± 10 | 77 ± 4 | 88 ± 4 |
| $\alpha_2$-Antiplasmin (%) | 70 ± 1 | 70 ± 4 | 93 ± 4 | 98 ± 8 | 74 ± 6 | 87 ± 3 |

Mean ± SEM; kU = 1000 IU; Haemostasis-Parameter (% with reference to base line)

EXAMPLE 7

Pharmacological Properties of K2P from *E. coli* in a Dog Model for Coronary Artery Thrombosis An experimental model for acute myocardial infarction in animals was chosen as an example in order to the measured values after injection with the control value before injection was carried out with the Wilcoxon Test for pair differences.

In order to describe the thrombolytic effect, the number of reperfused animals per dose-group (=reperfusion rate) as well as the time up to the reperfusion (=reperfusion time) was quoted. In addition, the wet weight of the residual thrombus still present 2 h after injection was measured and the number of animals with a re-occlusion after reperfusion (=re-occlusion rate) was determined. With the aid of a semi-logarithmic regression analysis of the dose-effect (reperfusion rates) relationships, the effective dose for a 50% reperfusion rate (=$ED_{50}$) was determined for each substance. The statistical comparison of the weights of the residual thrombi was carried out using the Wilcoxon-Mann-Whitney Test for unconnected random samples.

The plasma concentration of the t-PA activity was measured with a spectrophotometric test according to Verheijen et al., (Thromb. Haemost. 48, 266, 1982) modified according to Lill (Z. gesamte Inn. Med. 42, 478, 1987). A calculation programme for non-linear regression modified according to H. Y. Huang (Aero-Astronautics-Report 64, Rice University, USA, 1–30, 1969) was used to calculate the pharmacokinetic parameters. The parameters were calculated individually using a bi-exponential pharmacokinetic model after subtraction of the endogenous basal level of t-PA activity from the subsequent measured values.

The following results were obtained:

1. Pharmacodynamics in the Dog

K2P resulted in a dose-dependent reperfusion rate after intravenous injection. The maximum effect (reperfusion rate of 100%) was achieved after an injection of 200 kU/kg body weight. The dose with 100% success in reperfusion with Actilyse ® was 1,600 kU/kg body weight. A comparison of the $ED_{50}$ values yielded a 11.5-fold lower value for K2P ($ED_{50}$=83 kU/kg body weight) than for Actilyse ® ($ED_{50}$=961 kU/kg body weight). The administration of a placebo did not result in a reperfusion. The weight of the residual thrombus in the placebo animals was 9.6±1.6 mg (mean±SEM); K2P as well as Actilyse ® resulted in a statistically significant reduction in the weight of the residual thrombus with increasing doses in comparison to the placebo control. The reperfusion occurred with both fibrinolytic agents, as an average over all animals, after 25.9±3.5 min for K2P or after 24.2±6.2 min (Actilyse ®). Most of the dogs treated with K2P or Actilyse ® re-occluded after the reperfusion (Tab. 3)

2. Pharmacokinetics in the Dog

After intravenous injection of 200 kU/kg K2P or Actilyse ® it was seen that the fast phase of the decrease in the plasma concentration, expressed as $t_{\frac{1}{2}}\alpha$, was about a factor of 4.5 longer with K2P at 7.2±1.1 min than with Actilyse ® at 1.6±0.2 min (Tab. 4). The plasma concentration of K2P determined immediately after the end of the injection was about twice as high as that of Actilyse ®. The clearance of K2P from the plasma (plasma clearance =$Cl_{tot}$) was nine-fold slower than of Actilyse ®. Correspondingly, the area under the plasma concentration-time curve of K2P was approximately 9.5 times larger than that of Actilyse ®.

3. Fibrin Specificity in the Dog

Two hours after injection of K2P there was a dose-dependent slight reduction in the residual concentration of fibrinogen to 81±10% at the highest dose (200 kU/kg body weight). In contrast, the fibrinogen concentration was almost completely reduced to 3±0% after administration of the highest dose of Actilyse ® (1,600 kU/kg body weight) (Tab. 5). If one carries out a semi-logarithmic regression analysis of the dose-side-effect (fibrinogen reduction) relationship and determines the residual concentration of fibrinogen which corresponds to the $ED_{50}$ for thrombolytic effect, it results that for equipotent doses the residual content of fibrinogen was 92.5% with K2P compared to 38.6% with Actilyse ®. There is also a dose-dependent lowering of the residual contents of plasminogen and $\alpha_2$-antiplasmin 2 h after injection which is more pronounced with Actilyse ® than with K2P. Only the concentration of platelets is virtually uninfluenced by the two substances.

4. Influence on the Bleeding Time in the Dog

Figure 7:
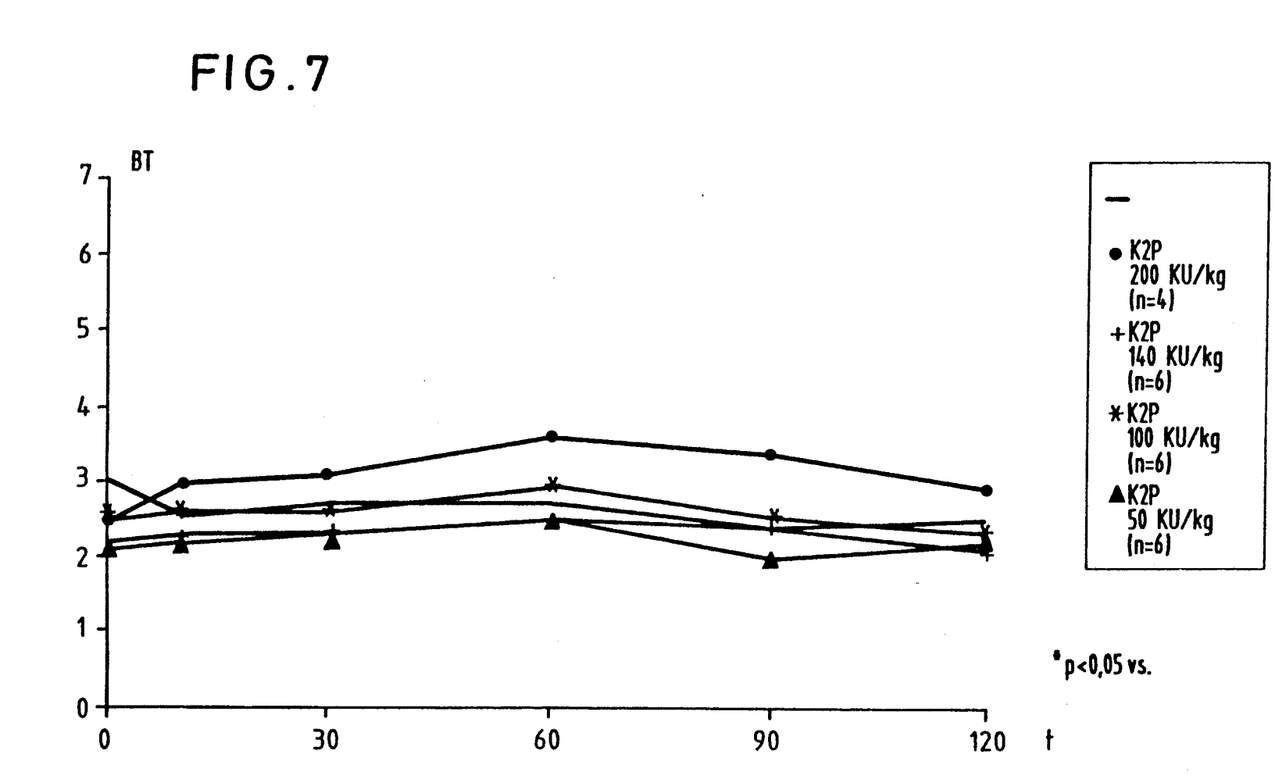
FIG. 7 shows the time course for Simplate bleeding time (BT) before and after an i.v. bolus injection of placebo or increasing doses of K2P in anaesthetised dogs.

The intravenous injection of K2P did not result in a statistically significant increase in the bleeding time in comparison with the control value before injection at all four doses investigated. In contrast, Actilyse ® increased the bleeding time which was statistically significant at doses of 1130 and 1600 kU/kg body weight (FIG. 6 and 7).

5. Overall assessment

In the described model for coronary artery thrombosis in dogs, K2P proved to be a thrombolytic agent which can achieve a 100% rate of reperfusion without a major influence on the fibrinogen concentration and without a significant increase in the bleeding time. K2P was clearly superior (factor of 11.5) in its thrombolytic potency after an intravenous bolus injection in comparison with Actilyse ® as state of the art. Furthermore, the investigation of the pharmacokinetic profile of K2P revealed that, in comparison with Actilyse ®, the clearance of K2P was nine-fold slower as an expression of the slower clearance from the plasma.

TABLE 3

Thrombolysis parameters in a model for coronary artery thrombosis in the dog after i.v. bolus injection (over 1 min) of placebo or increasing doses of Actilyse ® or K2P

| Substance | Dose (IU/kg body weight) | n | Reperfusion rate | Reperfusion time (min) | Wet weight of the residual thrombus (mg) | Re-occlusion rate |
|---|---|---|---|---|---|---|
| Placebo | — | 6 | 0/6 | / | 9.6 ± 1.2 | / |
| Actilyse ® | 1 600 000 | 6 | 6/6 | 28 ± 11 | 2,2 ± 0,7 | 4/6 |
|  | 1 130 000 | 6 | 4/6 | 14 ± 3 | 4,4 ± 0,5 | 4/4 |
|  | 800 000 | 6 | 2/6 | 35 ± 38 | 5,5 ± 0,4 | 1/2 |
|  | 200 000 | 6 | 0/6 | / | 8,8 ± 1,3 | / |
| K2P | 200 000 | 6 | 6/6 | 29 ± 6 | 2,5 ± 0,3 | 6/6 |
|  | 140 000 | 6 | 4/6 | 15 ± 6 | 4,4 ± 1,4 | 4/4 |
|  | 100 000 | 6 | 3/6 | 30 ± 14 | 7,4 ± 1,1 | 2/3 |
|  | 50 000 | 6 | 2/6 | 31 ± 4 | 5,5 ± 0,8 | 2/2 | mean ± SEM

TABLE 4

Pharmacokinetic parameters derived from computer calculations of plasma concentration-time data based on the t-PA activity in anaesthetized dogs after i.v. bolus injection of 200000 IU/kg body weight Actilyse ® or K2P

| Substance | $T_{\frac{1}{2}\alpha}$ (min) | $T_{\frac{1}{2}\beta}$ (min) | $C_{inj.}$ (IU/ml) | $V_c$ (ml/kg) | $Cl_{tot}$ (ml·kg$^{-1}$·min$^{-1}$) | $AUC_{extrapol.}$ (IU·ml$^{-1}$·h) |
|---|---|---|---|---|---|---|
| Actilyse ® | 1,6 | 14,6 | 1674 | 106,1 | 41,6 | 84,1 |
| (n = 6) | 0,2 | 6,6 | ±504 | ±37 | ±11,4 | ±23,8 |
| K2P | 7,2 | 15,0 | 3177 | 64,7 | 4,6 | 803 |
| (n = 6) | ±1,1 | ±4,3 | ±817 | ±19,7 | ±1,3 | 250 |
|  | (n = 4) |  |  |  |  |  |

Mean ± standard deviation
$V_c$ = Volume of distribution of the central compartment
$Cl_{tot}$ = Total plasma clearance
$AUC_{extrapol.}$ = "Area under the curve"; extrapolated area under the plasma concentration-time curve

TABLE 5

Coagulation parameters and number of thrombocytes 2 h after i.v. bolus injection (over 1 min) of placebo of increasing doses of Actilyse ® of K2P in a model for coronary artery thrombosis artery thrombosis in the dog

| Substance | Dose (IU/kg body weight) | n | Fibrinogen (%) | Plasminogen (%) | $\alpha_2$-Antiplasmin (%) | Number of platelets (%) |
|---|---|---|---|---|---|---|
| Placebo | — | 6 | 106 ± 2 | 103 (n = 4) | 92 ± 11 (n = 4) | 101 ± 3 |
| Actilyse ® | 1 600 000 | 6 | 3 ± 0 | 46 ± 2 | 19 ± 11 | 119 ± 10 |
|  | 1 130 000 | 6 | 16 ± 13 | 59 ± 6 | 45 ± 6 | 110 ± 10 |
|  | 800 000 | 6 | 86 ± 4 | 87 ± 3 | 64 ± 5 | 104 ± 6 |
|  | 200 000 | 6 | 97 ± 3 | 90 ± 3 | 86 ± 4 | 109 ± 4 |
| K2P | 200 000 | 6 | 81 ± 10 | 74 ± 8 | 40 ± 6 | 106 ± 8 |
|  | 140 000 | 6 | 93 ± 1 | 81 ± 1 | 50 ± 7 | 104 ± 5 |
|  | 100 000 | 6 | 92 ± 3 | 88 ± 3 | 77 ± 7 | 101 ± 3 |
|  | 50 000 | 6 | 95 ± 3 | 90 ± 2 | 84 ± 12 | 118 ± 11 |

Mean ± SEM
Values for coagulation and number of thrombocytes are expressed as % of the initial values before injection

We claim:

1. A thrombolytically active, non-glycosylated protein consisting of amino acid sequence:

```
  1 SYQGNSDCYF GNGSAYRGTH SLTESGASCL
                PWNSMILIGK VYTAQNPSAQ
 51 ALGLGKHNYC RNPDGDAKPW CHVLKNRRLT
                WEYCDVPSCS TCGLRQYSQP
101 QFRIKGGLFA DIASHPWQAA IFAKHRRSPG
                ERFLCGGILI SSCWILSAAH
151 CFQERFPPHH LTVILGRTYR VVPGEEEQKF
                EVEKYIVHKE FDDDTYDNDI
201 ALLQLKSDSS RCAQESSVVR TVCLPPADLQ
                LPDWTECELS GYGKHEALSP
251 FYSERLKEAH VRLYPSSRCT SQHLLNRTVT
                DNMLCAGDTR SGGPQANLHD
301 ACQGDSGGPL VCLNDGRMTL VGIISWGLGC
                GQKDVPGVYT KVTNYLDWIR
351 DNMRP
``` or said amino acid sequence with an additional, N-terminal methionine.

2. An isolated nucleic acid molecule which codes for the thrombolytically active, non-glycosylated protein of claim 1.

3. The isolated nucleic acid molecule of claim 2, having nucleotide sequence:

```
  1 ATGTCTTACCAAGGAAACAGTGACTCCTACTTTGGGAATGGGTCAGCCTACCGTGGCACG   60
 61 CACAGCCTCACCGAGTCGGGTGCCTCCTGCCTCCCGTGGAATTCCATGATCCTGATAGGC  120
121 AAGGTTTACACAGCACAGAACCCCAGTGCCCAGGCACTGGGCCTGGGCAAACATAATAC   180
181 TGCCGGAATCCTGATGGGGATGCCAAGCCCTGGTGCCACGTGCTGAAGAACCGCAGGCTG  240
241 ACGTGGGAGTACTGTGATGTGCCCTCCTGGTCCACCTGCGGCCTGAGACAGTACAGCCAG  300
301 CCTCAGTTTCGCATCAAAGGAGGGCTCTTCGCCGACATCGCCTCCCACCCCTGGCAGGCT  360
361 GCCATCTTTGCCAAGCACAGGAGGTCGCCCGGAGAGCGGTTCCTGTGCGGGGGCATACTC  420
421 ATCAGCTCCTGCTGGATTCTCTCTGCCGCCCACTGCTTCCAGGAGAGGTTTCCGCCCCAC  480
481 CACCTGACGGTGATCTTGGGCAGAACATACCGGGTGGTCCCTGGCGAGGAGGAGCAGAAA  540
541 TTTGAAGTCGAAAAATACATTGTCCATAAGGAATTCGATGATGACACTTACGACAATGAC  600
```

```
601  ATTGCGCTGCTGCAGCTGAAATCGGATTCGTCCCGCTGTGCCCAGGAGAGCAGCGTGGTC   660
661  CGCACTGTGTGCCTTCCCCCGGCGGACCTGCAGCTGCCGGACTGGACGGAGTGTGAGCTC   720
721  TCCGGCTACGGCAAGCATGAGGCCTTGTCTCCTTTCTATTCGGAGCGGCTGAAGGAGGCT   780
781  CATGTCAGACTGTACCCATCCAGCCGCTGCACATCACAACATTTACTTAACAGAACAGTC   840
841  ACCGACAACATGCTGTGTGCTGGAGACACTCGGAGCGGCGGGCCCCAGGCAAACTTGCAC   900
901  GACGCCTGCCAGGGCCATTCGGGAGGCCCCCTGGTGTGTCTGAACGATGGCCGCATGACT   960
961  TTGGTGGGCATCATCAGCTGGGGCCTGGGCTGTGGACAGAAGGATGTCCCGGGTGTGTAC   1020
1021 ACAAAGGTTACCAACTACCTAGACTGGATTCGTGACAACATGCGACCG     1068
```

4. Expression plasmid comprising the isolated nucleic acid molecule of claim 2.

5. Expression plasmid comprising the isolated nucleic acid molecule of claim 3.

6. A pharmaceutical composition comprising the thrombolytically active, non-glycosylated protein of claim 1 and a pharmaceutically acceptable carrier.

* * * * *